(12) United States Patent
Green et al.

(10) Patent No.: US 7,691,620 B2
(45) Date of Patent: Apr. 6, 2010

(54) ETHANOL PRODUCTION

(75) Inventors: Edward Green, Guildford (GB); Muhammad Javed, Dagenham (GB); Namdar Baghaei-Yazdi, London (GB)

(73) Assignee: Elsworth Biotechnology Limited, Guildford (GB)

( * ) Notice: Subject to any disclaimer, the term of this patent is extended or adjusted under 35 U.S.C. 154(b) by 0 days.

(21) Appl. No.: 11/717,004

(22) Filed: Mar. 13, 2007

(65) Prior Publication Data

US 2007/0292928 A1 Dec. 20, 2007

Related U.S. Application Data

(63) Continuation of application No. 10/700,472, filed on Nov. 5, 2003, now abandoned, which is a continuation of application No. 09/754,083, filed on Jan. 5, 2001.

(60) Provisional application No. 60/177,199, filed on Jan. 21, 2000.

(30) Foreign Application Priority Data

Jan. 6, 2000 (GB) .................................. 0000185.9

(51) Int. Cl.
*C12N 1/20* (2006.01)
*C12N 9/54* (2006.01)
*C12P 7/06* (2006.01)

(52) U.S. Cl. .............................. 435/252.31; 435/252.5; 435/161; 435/221

(58) Field of Classification Search ........................ None
See application file for complete search history.

(56) References Cited

U.S. PATENT DOCUMENTS 5,182,199 A * 1/1993 Hartley ........................ 435/162
5,916,787 A   6/1999 Ingram et al.

FOREIGN PATENT DOCUMENTS

WO  WO 88/09379   12/1988
WO  WO 95/27064   10/1995

OTHER PUBLICATIONS

R. San Martin et al., "Pathways of Ethanol Production from Sucrose by a Mutant Thermophilic *Bacillus* in Continuous Culture," Journal of General Microbiology (1993) 139, pp. 1033-1040.
V. N. Danilevich et al., "Construction of Recombinant Plasmids for Efficient Expression of the Pyruvate Decarboxylasse Gene (*pdk*) from *Zymomonas mobilis* and *Bacillus subtilis*," Molecular Biology (1994), vol. 28, No. 1, pp. 158-166.
B. S. Hartley et al., "Development and Economics of a Novel Thermophilic Ethanol for Ethanol Production," Biotech (1983), pp. 895-905.
L. O. Ingram, 'Metabolic Engineering of Bacteria for Ethanol Production,' Biotechnology and Bioengineering (1998), vol. 58, Nos. 2-3.
M. Payton, "Production of Ethanol by Thermophilic Bacteria," Trends in Biotechnology (1984), vol. 2, No. 6, pp. 153-158.
H. Danner at al., "*Bacillus Stearotheromophilus* for the Thermophilic Production of L-Lactic Acid," Applied Biochemistry and Biotechnology, Apr. 1998, vol. 70-72, pp. 895-903.
S. Murakami et al., "DNA Encoding *Bacillus* sp. L-Lactic Acid Dehydrogenase," Online Database EMBL (1997).
Guagliardi et al., Int. J. Biochem. Cell Biol. 1996, vol. 28(2):239-246.
Conway et al., 197, J. Bacteriol. vol. 169(3):949-954.
H. Li at al., Biochemistry, 1999, vol. 38:10004-10012.
Bingham et al., J. Gen. Microbiol., 1980, 119:109-115.
Payton et al., FEMS Microbial let. 1985, 26, pp. 333-336.

* cited by examiner

*Primary Examiner*—Delia M Ramirez
*Assistant Examiner*—Md. Younus Meah
(74) *Attorney, Agent, or Firm*—Banner & Witcoff, Ltd.

(57) ABSTRACT

Production of ethanol in a thermophilic bacterium can be achieved by transformation of the bacterium with a heterologous gene encoding pyruvate decarboxylase. The bacterium comprises native alcohol dehydrogenase function and does not comprise a gene encoding a functional lactate dehydrogenase. The bacterium may be grown at elevated temperatures to allow the ethanol to be conveniently removed in a vaporized form from the fermentation medium. Traditional mesophilic microorganisms are incapable of growth at the envisioned elevated temperatures.

7 Claims, 10 Drawing Sheets

LDH Gene Inactivation by Double-Crossover Recombination

LDH Gene Inactivation and Heterologous *PDC* Gene Expression

Figure 6
Expression of PDC
Construct 1 (cloned in pBST22)
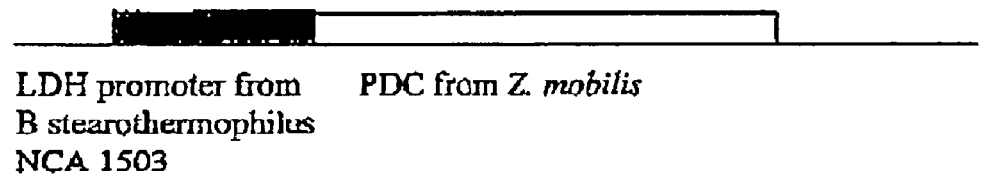
LDH promoter from
B stearothermophilus
NCA 1503
PDC from Z. mobilis
Construct 2 (cloned in pFC1)
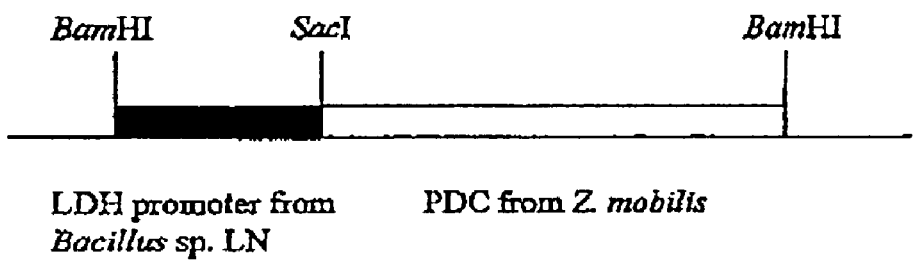
LDH promoter from
Bacillus sp. LN
PDC from Z. mobilis
Construct 3 (cloned in pFC1)
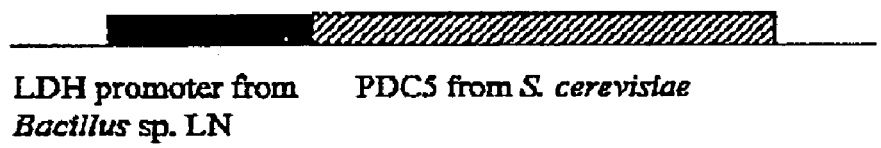
LDH promoter from
Bacillus sp. LN
PDC5 from S. cerevisiae Figure 7.    LDH promoter sequence from *Bacillus* LN

AGGGCAATCTGAAAGGAAGGGAAAATTCCTTTCGGATTGTCCTTTTAGTTATTTTTATGG  - 60

GGAGTGAATATTATATAGGCATTACGGAAATGATAATGGCAGAGTTTTTTCATTTATTAG  - 120

<u>ACTGCTTGATGTAATTGGATGTGATGATACAAAAATAATGTTG</u>TGTAAACAAAATGTTAA  - 180

CAAAAAGACAAATTTCATT<u>CATAGTTGATACTTGATAAAGATTGTGAAATAATGCACAA</u>  - 240

TATATCAATGTATGAGCAGTTTCACAAATTCATTTTTTGGAAAGGATGACAGACAGCG\*AT  - 300

G underlined: putative promoter sequences
bold: putative ribosome binding site
\*:     start codon Figure 10          Construction of an Artificial PDC operon
Construct 4
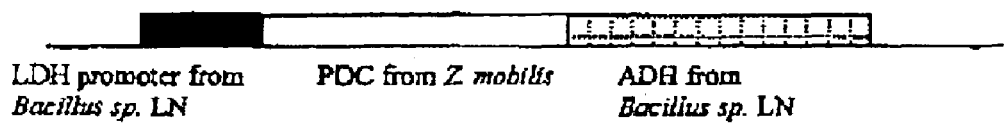
LDH promoter from        PDC from Z. mobilis        ADH from
Bacillus sp. LN                                     Bacillus sp. LN
Construct 5
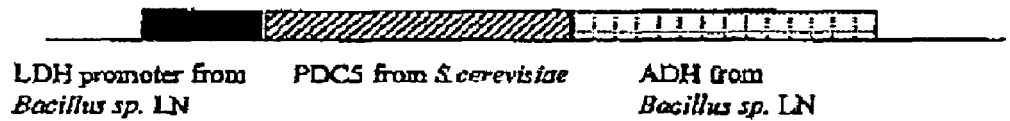
LDH promoter from        PDC5 from S. cerevisiae    ADH from
Bacillus sp. LN                                     Bacillus sp. LN

ETHANOL PRODUCTION

This invention relates to the production of ethanol as a product of bacterial fermentation. In particular, the invention relates to ethanol production by thermophilic strains of *Bacillus* sp.

Many bacteria have the natural ability to metabolise simple sugars into a mixture of acidic and neutral fermentation products via the process of glycolysis. Glycolysis is the series of enzymatic steps whereby the six carbon glucose molecule is broken down, via multiple intermediates, into two molecules of the three carbon compound pyruvate. The glycolytic pathways of many bacteria produce pyruvate as a common intermediate. Subsequent metabolism of pyruvate results in a net production of NADH and ATP as well as waste products commonly known as fermentation products. Under aerobic conditions, approximately 95% of the pyruvate produced from glycolysis is consumed in a number of short metabolic pathways which act to regenerate $NAD^+$ via oxidative metabolism, where NADH is typically oxidised by donating hydrogen equivalents via a series of steps to oxygen, thereby forming water, an obligate requirement for continued glycolysis and ATP production.

Under anaerobic conditions, most ATP is generated via glycolysis. Additional ATP can also be regenerated during the production of organic acids such as acetate, $NAD^+$ is regenerated from NADH during the reduction of organic substrates such as pyruvate or acetyl CoA. Therefore, the fermentation products of glycolysis and pyruvate metabolism include organic acids, such as lactate, formate and acetate as well as neutral products such as ethanol.

The majority of facultatively anaerobic bacteria do not produce high yields of ethanol either under aerobic or anaerobic conditions. Most facultative anaerobes metabolise pyruvate aerobically via pyruvate dehydrogenase (PDH) and the tricarboxylic acid cycle (TCA). Under anaerobic conditions, the main energy pathway for the metabolism of pyruvate is via pyruvate-formate-lyase (PFL) pathway to give formate and acetyl-CoA. Acetyl-CoA is then converted to acetate, via phosphotransacetylase (PTA) and acetate kinase (AK) with the co-production of ATP, Or reduced to ethanol via acetaldehyde dehydrogenase (AcDH) and alcohol dehydrogenase (ADH). In order to maintain a balance of reducing equivalents, excess NADH produced from glycolysis is re-oxidised to $NAD^+$ by lactate dehydrogenase (LDH) during the reduction of pyruvate to lactate. NADH can also be re-oxidised by AcDH and ADH during the reduction of acetyl-CoA to ethanol but this is a minor reaction in cells with a functional LDH. Theoretical yields of ethanol are therefore not achieved since most acetyl CoA is converted to acetate to regenerate ATP and excess NADH produced during glycolysis is oxidised by LDH.

Ethanologenic organisms, such as *Zymomonas mobilis* and yeast, are capable of a second type of anaerobic fermentation commonly referred to as an alcoholic fermentation in which pyruvate is metabolised to acetaldehyde and $CO_2$ by pyruvate decarboxylase (PDC). Acetaldehyde is then reduced to ethanol by ADH regenerating $NAD^+$ Alcoholic fermentation results in the metabolism of 1 molecule of glucose to two molecules of ethanol and two molecules of $CO_2$. The genes which encodes both of these enzymes in *Z. mobilis* have been isolated, cloned and expressed recombinantly in hosts capable of producing high yields of ethanol via the synthetic route described above. For example; U.S. Pat. No. 5,000,000 and Ingram et al (1997) *Biotechnology and Bioengineering* 58, Nos. 2 and 3 have shown that the genes encoding both PDC (pdc) and ADH (adh) from *Z. mobilis* can be incorporated into a "pet" operon which can be used to trans form *Escherichia coli* strains resulting in the production of recombinant *E. coli* capable of co-expressing the *Z. mobilis* pdc and adh. This results in the production of a synthetic pathway re-directing *E. coli* central metabolism from pyruvate to ethanol during growth under both aerobic and anaerobic conditions. Similarly, U.S. Pat. No. 5,554,520 discloses that pdc and adh from *Z. mobilis* can both be integrated via the use of a pet operon to produce Gram negative recombinant hosts, including *Erwina, Klebsiella* and *Xanthomonas* species, each of which expresses the heterologous genes of *Z. mobilis* resulting in high yield production of ethanol via a synthetic pathway from pyruvate to ethanol.

U.S. Pat. No. 5,482,846 discloses the simultaneous transformation of Gram positive *Bacillus* sp with heterologous genes which encode both the PDC and ADH enzymes so that the transformed bacteria produce ethanol as a primary fermentation product. There is no suggestion that the bacteria may be transformed with the pdc gene alone.

A key improvement in the production of ethanol using biocatalysts can be achieved if operating temperatures are increased to levels at which the ethanol is conveniently removed in a vapourised form from the fermentation medium. However, at the temperatures envisioned, traditional mesophilic microorganisms, such as yeasts and *Z. mobilis*, are incapable of growth. This has led researchers to consider the use of thermophilic, ethanologenic bacteria as a functional alternative to traditional mesophilic organisms. See EP-A-0370023.

The use of thermophilic bacteria for ethanol production offers many advantages over traditional processes based upon mesophilic ethanol producers. Such advantages include the ability to ferment a wide range of substrates, utilising both cellobiose and pentose sugars found within the dilute acid hydrolysate of lignocellulose, as well as the reduction of ethanol inhibition by continuous removal of ethanol from the reaction medium using either a mild vacuum or gas sparging. In this way, the majority of the ethanol produced may be automatically removed in the vapour phase at temperatures above 50° C. allowing the production phase to be fed with high sugar concentrations without exceeding the ethanol tolerance of the organism, thereby making the reaction more efficient. The use of thermophilic organisms also provides significant economic savings over traditional process methods based upon lower ethanol separation costs.

The use of facultative anaerobes also provides a number of advantages in allowing a mixed aerobic and anaerobic process. This facilitates the use of by-products of the anaerobic phase to generate further catalytic biomass in the aerobic phase which can then be returned to the anaerobic production phase.

The inventors have produced sporulation deficient variants of a thermophilic, facultatively anaerobic, Gram-positive bacterium which exhibit improved ethanol production-related characteristics.

This approach has a number of important advantages over conventional processes using both traditional and recombinant mesophilic bacteria, including simplification of the transformation process by using only the pdc gene of *Z. mobilis* in strains that already produce ethanol and have a 'native' adh gene. Expression of pdc has resulted in a significant increase in ethanol production by the recombinant organism and has unexpectedly improved the organism's growth characteristics. Recombinant microorganisms, which prior to transformation with the pdc gene were highly unstable and difficult to culture, show significant increases in growth and survival rates both aerobically and anaerobically as well as an increase in the rate of ethanol production near to theoretical yields.

Accordingly, a first aspect of the invention relates to a Gram-positive bacterium which has been transformed with a heterologous pdc gene, but which has solely a native alcohol dehydrogenase function. The gene may encode a functional equivalent of pyruvate decarboxylase Functional equivalents of pyruvate decarboxylase include expression products of insertion and deletion mutants of natural pdc gene sequences.

It is possible that organisms which carry out glycolysis or a variant thereof can be engineered, in accordance with the present invention, to convert as much as 67% of the carbon in a sugar molecule via glycolysis and a synthetic metabolic pathway comprising enzymes which are encoded by heterologous pdc and native adh genes. The result is an engineered organism which produces ethanol as its primary fermentation product.

The Gram-positive bacterium is preferably a *Bacillus*. The bacterium may be a thermophile. Where the Gram-positive bacterium is a *Bacillus* it is preferably selected from *B. stearothermophilus; B. calvodex; B. caldotenax; B. thermoglucosidasius, B. coagulans, B. licheniformis, B. thermodenitrificans*, and *B. caldolyticus*.

A gene encoding lactate dehydrogenase may be inactivated in the Gram-positive bacterium of the invention. For example, the lactate dehydrogenase gene may be inactivated by homologous recombination.

The heterologous pdc gene may be from *Zymomonas* sp, preferably *Z. mobilis* or may be from yeast e.g. the *S. cerevisae* pdc 5 gene.

The heterologous gene may be incorporated into the chromosome of the bacterium. Alternatively, the bacterium may be transformed with a plasmid comprising the heterologous gene. Preferably the bacterium is transformed using plasmid is pFC1, more preferably with pFC1-PDC1. The invention includes Gram-positive bacteria, preferably a *Bacillus* sp including the operon of the invention. The *Bacillus* sp may be selected from *B. stearothermophilus; B. calvodex; B. caldotenax, B. thermoglucosidasius, B. coagulans, B. licheniformis, B. thermodenitrificans*, and *B. caldolyticus*. The operon may be incorporated into the genome of the *Bacillus*. Multiple copies of the PDC operon may be incorporated into the genome.

In a preferred embodiment of the present invention the Gram-positive bacteria has the heterologous gene operatively linked to the lactate dehydrogenase promoter from *Bacillus* strain LN (NCIMB accession number 41038) so that the heterologous gene is under the control of the promoter. The sequence of the promoter region from strain LN is shown in FIG. 8.

The invention also provides strains LN (NCIMB accession number 41038); LN-T (E31, E32); TN (NCIMB accession number 41039); TN-P1; TN-P3; LN-S (J8) (NCIMB accession number 41040); LN-D (NCIMB accession number 41041); LN-D11 and LN-P1.

According to another aspect of the invention, there is provided a recombinant, sporulation deficient, thermophilic *Bacillus* which grows at greater than 50° C. The *Bacillus* is preferably not *B. licheniformis*.

A second aspect of the present invention relates to a method of producing ethanol using bacteria of the invention maintained under suitable conditions.

The method may be operated at a temperature between 40-75° C.; preferably at a temperature of 52-65° C.; most preferably at a temperature of 60-65° C.

The present invention also relates to a method of producing L-lactic acid using strain LN.

The present invention also provides a nucleic acid molecule comprising the lactate dehydrogenase promoter of strain LN (NCIMB accession number 41038). The sequence of a nucleic acid molecule comprising the lactate dehydrogenase promoter of strain LN is shown in FIG. 7. Preferably the nucleic acid molecule comprises a functional fragment of the nucleic acid sequence shown in FIG. 7. A functional fragment is defined as a fragment that function as a promoter and enables the expression of an operably linked gene.

The present invention also provides plasmid pFC1. The structure of this plasmid is shown schematically in FIG. 8

The present invention also provides plasmid pFC1-PDC1. The structure of this plasmid is shown schematically in FIG. 9.

The production of recombinant bacteria in accordance with the invention will now be described, by way of example only, with reference to the accompanying drawings, FIGS. 1 to 10 in which.

Figure 8:
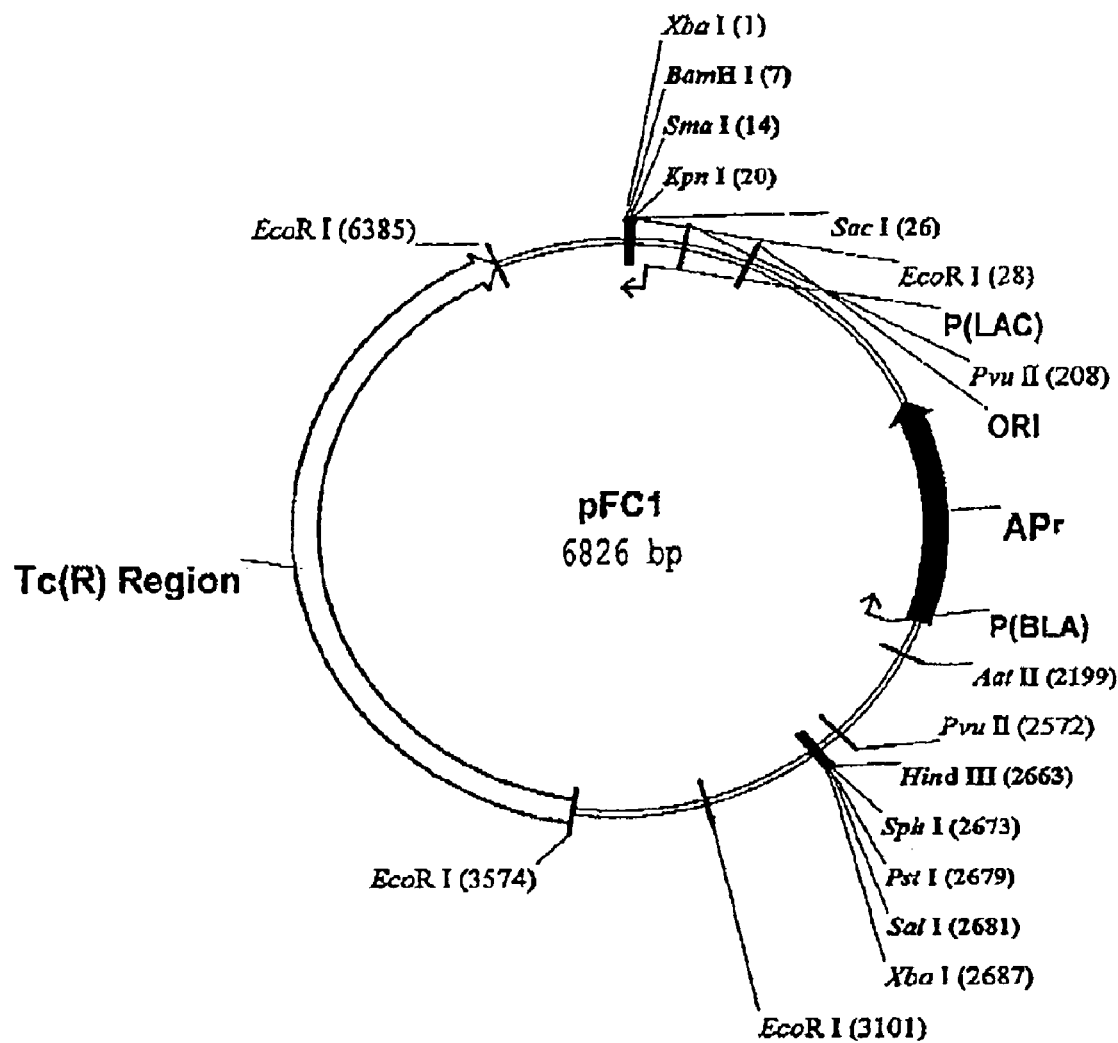
Figure 9:
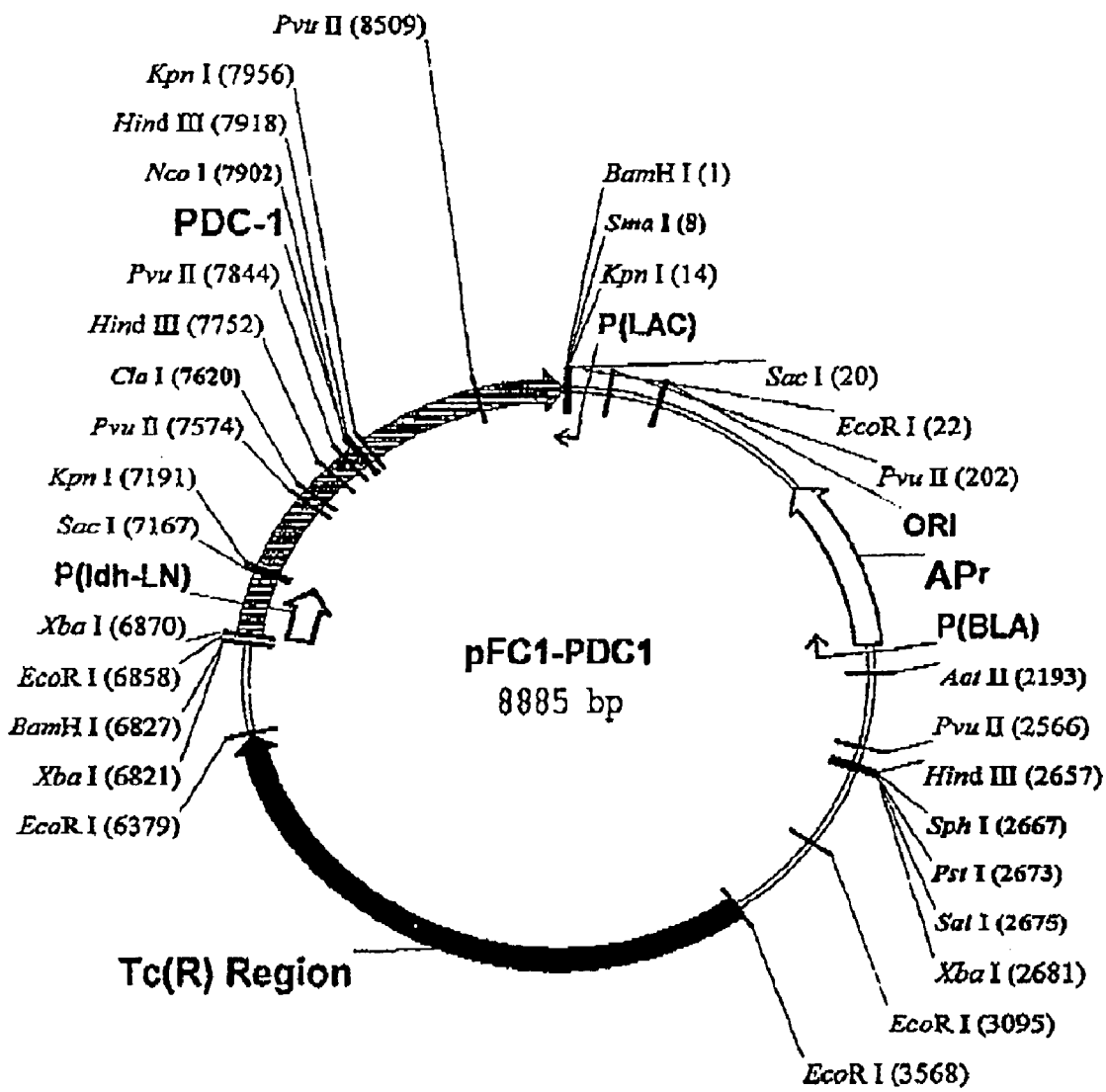

FIG. 6 provides details about the PDC gene and promoter construct;

FIG. 7 provides sequence data about the LDH promoter from *Bacillus* LN (SEQ ID NO:5);

FIG. 8 is a schematic disown of the replicative plasmid pFC1;

FIG. 9 is a schematic diagram of the PDC construct 2 coned into the pFC1 plasmid; and FIG. 10 shows the construction of an artificial PDC operon.

The inventors initiated a strain development program to overcome inherent strain limitations in respect of ethanol production, such as instability and sporulation under adverse conditions. Physiological manipulation and selection for strains with superior growth characteristics has been achieved in continuous culture, whereas a more targeted genetic approach has been used to engineer strains with greater stability and superior production characteristics.

Figure 1:
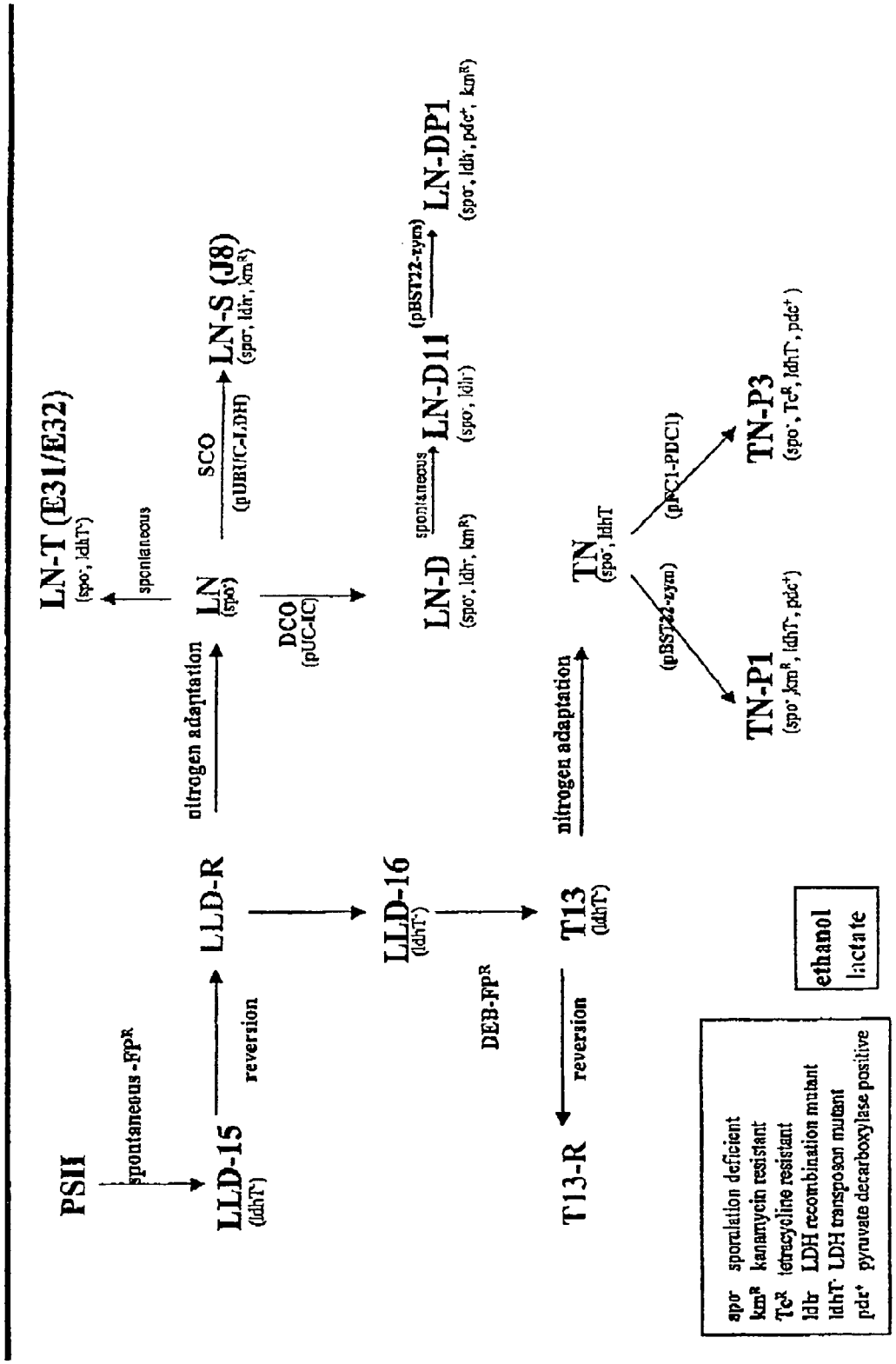
FIG. 1 is a schematic representation showing the production of bacterial strains of the invention.
Figure 2:
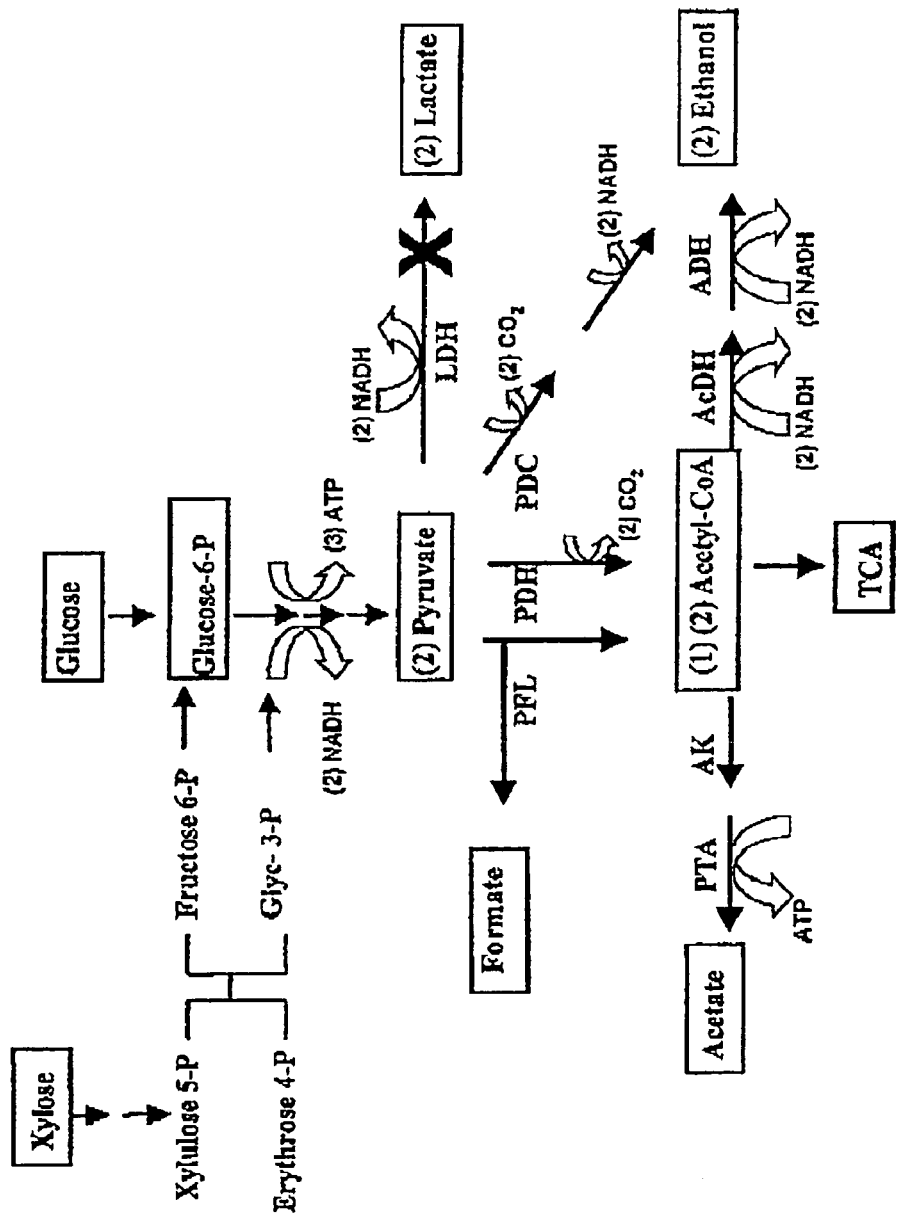
FIG. 2 illustrates the metabolic pathway whereby sugars are metabolised to produce ethanol by bacterial strains of the invention.

In accordance with FIG. 1, all strains were ultimately derived from a previously isolated *Bacillus* isolate PSII, a novel, thermophilic, Gram-positive, spore-forming, facultative anaerobe. PSII ferments a wide range of organic compounds from sugars, including hemicelluloses, to organic acids such as acetate, formate and lactate and small amounts of ethanol at temperatures between 50° C. and 70° C.

*Bacillus* strains LLD-15, LLD-R, LLD-16 and T13 have been described in EP-A-0370023 and by Amartey et al, (1999) *Process Biochemistry* 34 No. 3 pp. 289-294. Strain LLD-15 (NCIMB12428) arose during attempts to obtain mutants of *Bacillus stearothermophilus* strain NCA 1503 lacking L-LDH activity by selecting for suicide substrate resistance (Payton and Hartley (1984) *Trends in Biotechnology*, 2 No. 6). Strain LLD-15 was assumed to be a variant of *B. stearothermophilus* NCA1503, but is, in fact, derived from PS11. Strain LLD-R arises spontaneously and reproducibly from strain LLD-15 and is selected on plates or during continuous cultures under which it grows more rapidly (i.e. at low pH in media containing sugars, acetate and formate). LLD-R produces L-lactate anaerobically and contains high levels of L-LDH, so is therefore, clearly a wild type revertant of the non-lactate-producing LLD-15 lesion.

Bacillus strain T13 is an L-lactate deficient mutant of strain LLD-R. Isolation and characterisation of this mutant strain has been described previously by, Javed. M. PhD Thesis, Imperial College, London. Thus, Bacillus strains LLD-15, LLD-16 and T13 are mutants of the original isolate, PSII in which the ldh gene has been inactivated either via spontaneous mutation or by chemical mutagenesis and the major fermentation product, unlike PSII, is ethanol. The lactate dehydrogenase gene mutation in LLD-15, LLD-16 and T13 results from the insertion of a transposon into the coding region of the lactate dehydrogenase gene resulting in ldhT geno-type. All three strains are inherently unstable in high sugar concentrations (>2%) and revert back to lactate producing strains. Strains T13 and LLD-15 revert to T13-R and LLD-R, respectively. Strains LLD-15, LLD-R, LLD-16 and T13 also tend to sporulate under adverse growth conditions such as changes in pH, temperature and medium compositions, and during periods of nutrient starvation. Since sporulation often leads to culture washout in a continuous system, these strains are not suitable for large scale industrial use in which process parameters fluctuate.

EXAMPLE 1

Production of LN

Bacillus strain LN was produced from LLD-R as a spontaneous sporulation mutant which arose during nitrogen adaptation in continuous culture. Strain LN is more robust than the parental strains LLD-15 and LLD-R under vigorous industrial conditions such as low pH, high sugar concentrations and in crude hydrolysate feed stocks and is more amenable to plasmid transformation. Strain LN is sporulation deficient (spo⁻) and is particularly suitable for the production of high pity L-lactic acid, producing up to 0.4 g of L-lactate/g of glucose at 65° C. This strain is sensitive to kanamycin concentrations in excess of 5 µg/ml and an ideal host for genetic manipulation (ldh inactivation and heterologous gene expression). Strain LN has been deposited under the terms of the Budapest Treaty under accession No. NCIMB 41038.

EXAMPLE 2

Production of Strain LN-T (E31/E32)

Strains E31 and E32 are spontaneous transposon mutants from strain LN. Both strains are lactate deficient and produce up to 0.5 g of ethanol/g of glucose at 65° C. They are non-sporulating and as such more amenable to genetic manipulation than T13.

EXAMPLE 3

Production of Strain LN-S (J8)

Figure 3:
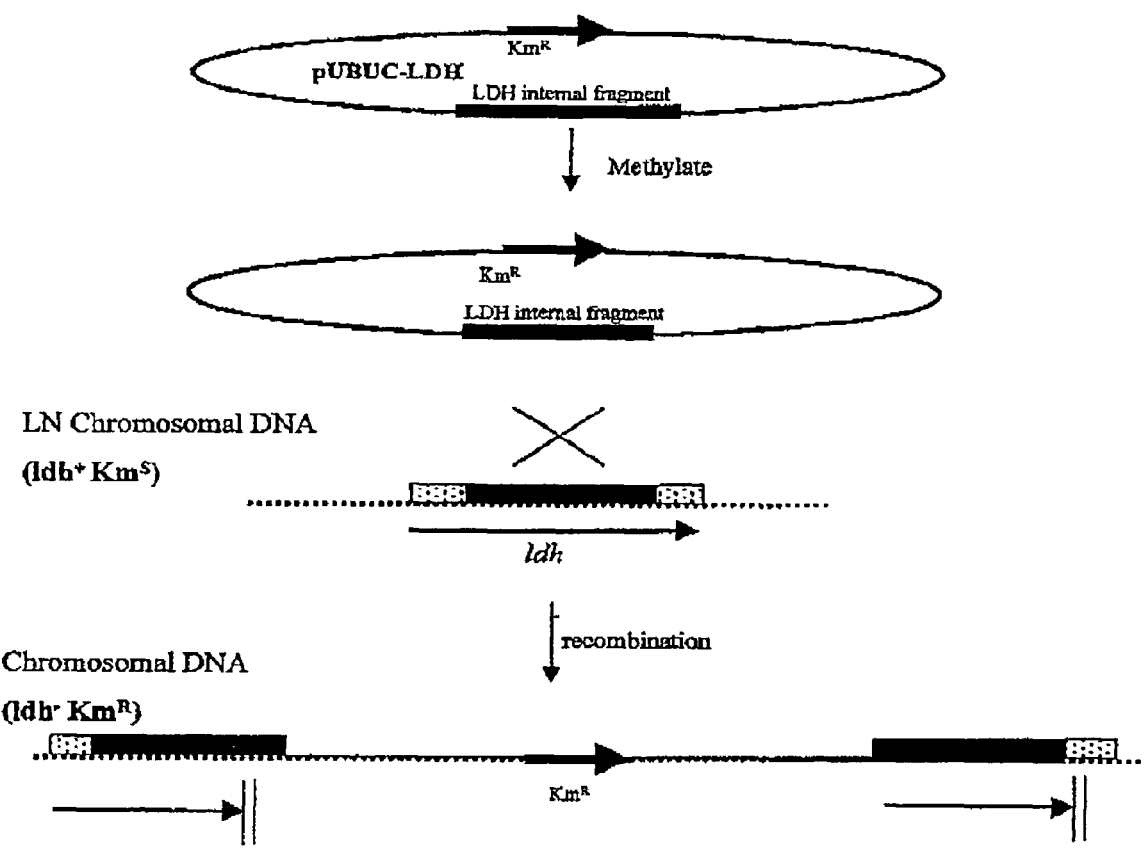
FIG. 3 is a schematic representation illustrating the method of LDH gene inactivation by single crossover recombination.

Strain LN-S (J8) was produced by a single crossover homologous recombination event between pUBUC-LDH a temperature sensitive, non-replicative plasmid harbouring an internal region of the ldh gene and the ldh gene on the chromosome (see FIG. 3). This resulted in inactivation of the ldh gene and a lactate negative phenotype. This strain is also sporulation deficient and resistant to kanamycin. It is stable in relatively high sugar concentrations in continuous culture (with 10 g/L of residual sugar), it has good growth characteristics and produces relatively high yields of ethanol. For example, in continuous culture at pH 7.0, 65° C., dilution rate of 0.1 h$^{-1}$, and 50 g/L glucose feed, the cells produce up to 20 g/L of ethanol (i.e. 0.4 g of ethanol/g of glucose utilised) for 200 hours or more without any drop in ethanol yield.

Strain LN-S (J8) has been deposited with the NCIMB under the terms of the Budapest Treaty under accession number NCIMB 41040.

EXAMPLE 4

Production of Strain LN-D

Figure 4:
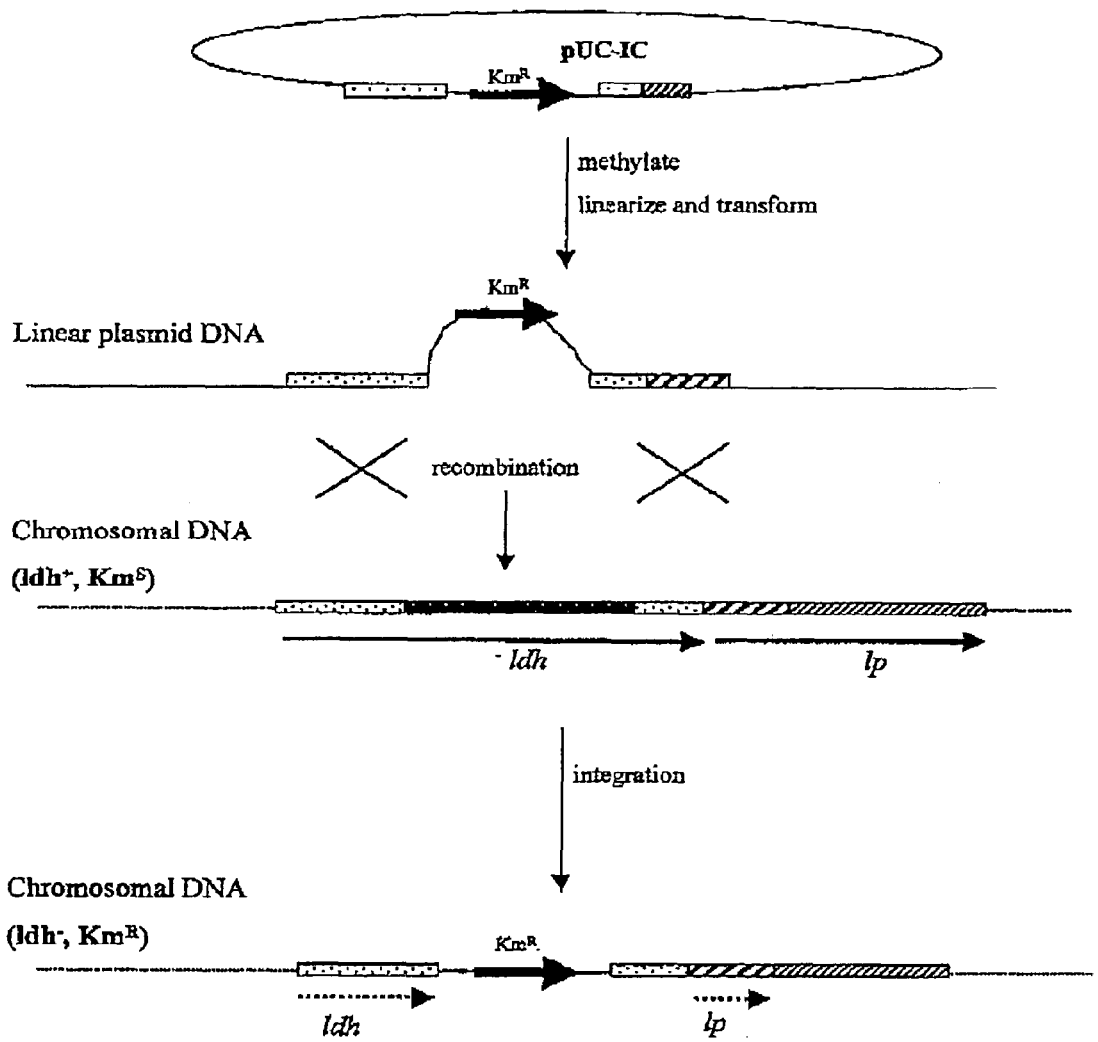
FIG. 4 is a schematic representation illustrating the method of LDH gene inactivation by double crossover recombination.

This strain was produced by a double crossover homologous recombination event between a linear insertion cassette and the ldh gene from strain LN (see FIG. 4). The insertion cassette (pUC-IC) is a non-replicating pUC18 plasmid harbouring a kanamycin resistance gene flanked by the ldh and lactase permease (lp) gene sequences. Recombination inactivated both the ldh and lp genes resulting in a lactate negative phenotype. This strain is also sporulation deficient and resistant to kanamycin. Strain LN-D can tolerate high sugar concentrations (with up to 10 g/L of residual sugar), it has good growth characteristics and produces relatively high yields of ethanol. For example, in continuous culture at pH 7.0, 52° C., dilution rate of 0.1 h$^{-1}$, and 50 g/L glucose feed, the cells produce up to 20 g/L of ethanol (i.e. 0.4 g of ethanol/g of glucose utilised) for 200 hours or more without any drop in ethanol yield or cell viability. Furthermore, kanamycin selection was not required to maintain the ldh gene inactivation.

Strain LN-D has been deposited with the NCIMB under the terms of the Budapest Treaty under accession number NCIMB 41041.

EXAMPLE 5

Production of Strain LN-D11

The resistance of strain LN-D to kanamycin was cured after repeated subculture to produce strain LN-D11. This strain is lactate negative, sporulation deficient and sensitive to kanamycin concentrations in excess of 5 µg/ml. Strain LN-D11 can tolerate high sugar concentrations (with up to 10 g/L of residual sugar), it has good growth characteristics and produces relatively high yields of ethanol. For example, in continuous culture at pH 7.0, 52° C., dilution rate of 0.1 h$^{-1}$, and 50 g/L glucose feed, the cells produce up to 20 g/L of ethanol (i.e. 0.4 g of ethanol/g of glucose utilised) for 200 hours or more without any drop in ethanol yield or cell viability. This strain is an ideal host for heterologous gene expression.

EXAMPLE 6

Production of Strain LN-DP1

Strain LN-DP1 was produced from strain LN-D11 after transformation with the replicative plasmid pBST22-zym (also referred to as pZP1). The backbone of this vector is pBST22 (originally developed by Liao et al (1986) PNAS (USA) 83: 576-580) with the entire pdc gene from Z. mobilis under the control of the ldh promoter sequence from B. stearothermophilus NCA 1503. Strain LN-DP1 is sporulation deficient; kanamycin resistant, lactate negative and contains the heterologous pdc gene from Z. mobilis. Strain LN-DP1 can utilise high sugar concentrations, it has good growth characteristics and produces relatively high yields of ethanol. For example, in continuous culture at pH 7.0, 60° C., dilution rate of 0.1 h$^{-1}$, and 50 g/L glucose feed, the cells produce up to 25 g/L ethanol (i.e. 0.5 g of ethanol/g of glucose utilised) for 200 hours or more without any drop in ethanol yield.

EXAMPLE 7

Production of Strain TN

Strain TN arose spontaneously from T13 during nitrogen adaptation in continuous culture. This strain is more robust than the parental strain under vigorous industrial conditions (i.e. low pH, high sugar concentrations, and in crude hydrolysate feed stocks) and is more amenable to plasmid transformation, making it an ideal host for genetic engineering. Strain TN is sporulation deficient and lactate negative (the ldh gene has been inactivated by transposon mutagenesis into the coding region of the ldh gene). Strain TN is a good ethanol producer on dilute sugar feeds. For example, in continuous culture at pH 7.0, 70° C., dilution rate of 0.1 h$^{-1}$, and 20 g/L glucose, the cells produce up to 8 g/L ethanol (i.e. 0.4 g of ethanol/g of glucose utilised) for 100 hours or more without any drop in ethanol yield. This strain is sensitive to kanamycin concentrations in excess of 5 µg/ml and an ideal host for genetic manipulation.

Strain TN has been deposited at the NCIMB under the terms of the Budapest Treaty under accession number NCIMB 41039.

EXAMPLE 8

Production of Strain TN-P1

Strain TN-P1 was produced from strain TN after transformation with the replicative plasmid pBST22-zym. As previously described, pBST22-zym was produced by the incorporation of a pdc gene in vector pBST22. The transformation efficiency of TN was 10-fold higher with pBST22-zym than pBST22 and the colony size of the transformants were significantly larger indicating that pdc expression conferred a growth advantage to the cells.

TN-P1 is also more stable and a better ethanol producer than TN, especially in sugar concentrations greater than 20 g/L. For example, in continuous culture controlled at pH 7.0, 52° C. with a dilution rate of 0.1 h$^{-1}$, and a sugar feed containing 20-50 g/L, strain TN-P1 produced up to 0.5 g ethanol/g sugar utilised for 600 hours with no significant drop in yield or cell viability. In addition, in continuous culture controlled at pH 7.0, 52° C. with a dilution rate of 0.1 h$^{-1}$, and a wheat crude hydrolysate feed, TN-P1 produced 0.4 g ethanol/g sugar utilised in for 400 hours with no significant drop in ethanol yield or culture viability.

Plasmid selection in strain TN-P1 was first maintained with kanamycin but the plasmid was found to be relatively stable without selection and no significant plasmid loss was detected after 300 hours of continuous culture. The plasmid and PDC enzyme were found to be relatively stable at high temperatures. In continuous culture controlled at pH 7.0, with a dilution rate of 0.1 h$^{-1}$, and a glucose feed of 30 g/L, there was no significant drop in ethanol yield or culture viability when the growth temperature was increased from 52 to 60° C.

EXAMPLE 9

Production of Strain TN-P3

Strain TN-P3 was produced from strain TN after transformation with the replicative plasmid pFC1-PDC1. The backbone of this vector is pFC1 (FIG. 8) which was formed from a fusion of pAB124 (Bingham et al., Gen. Microbiol., 114, 401-408, 1979) and pUC18. The pdc gene was amplified from Z. mobilis chromosomal DNA by PCR using the following primers. The restriction sites BamHI and SacI (bold) were introduced into the amplified gene.

```
5'-GAGCTCGCAATGAGTTATACTGTC-3'
(SEQ ID NO: 1)

5'-GGATCCCTAGAGGAGCTTGTTA-3'
(SEQ ID NO: 2)
```

The ldh promoter was amplified by PCR from Bacillus LN using the following primers. The restriction sites SacI and BamHI (underlined) were introduced into the amplified sequence.

```
5'-GGATCCGGCAATCTGAAAGGAAG-3'
(SEQ ID NO: 3)

5'-GAGCTCTCATCCTTTCCAAAA-3'
(SEQ ID NO: 4)
```

The ldh promoter sequence and pdc gene were digested with SacI and BamHI and then ligated together (FIG. 6). The construct was then digested with BamHI and ligated into BamHI digested pFC1 to form plasmid pFC1-PDC1 (FIG. 9).

Strain TN-P3 is a good ethanol producer and produces yields in excess of 0.45 g ethanol/g sugar at temperatures between 50 and 60° C.

Gene Inactivation

Single-Crossover Recombination (SCO) (FIG. 3)

SCO or Campbell-type integration was used for directed ldh gene inactivation. An internal fragment (700 bp) of the target gene (ldh) was first cloned into pUBUC to form pUBUC-LDH.

Plasmid pUBUC is a shuttle vector for DNA transfer between Escherichia coli and Bacillus strains LN and TN and was formed from the fusion of pUB110 and pUC18. This vector contains a selectable marker that confers resistance to kanamycin and a Gram-positive and Gram-negative replicon. The plasmid is temperature sensitive in Bacillus and cannot replicate above 54° C.

Plasmid pUBUC-LDH was first methylated (in vivo) and then transformed into the host strain (LN) at the permissible temperature (50° C.) for plasmid propagation. The growth temperature was then increased to 65° C., preventing plasmid replication and integrants were selected using kanamycin. Integration of the plasmid DNA into the ldh gene resulted in gene inactivation and a lactate negative phenotype.

Figure 5:
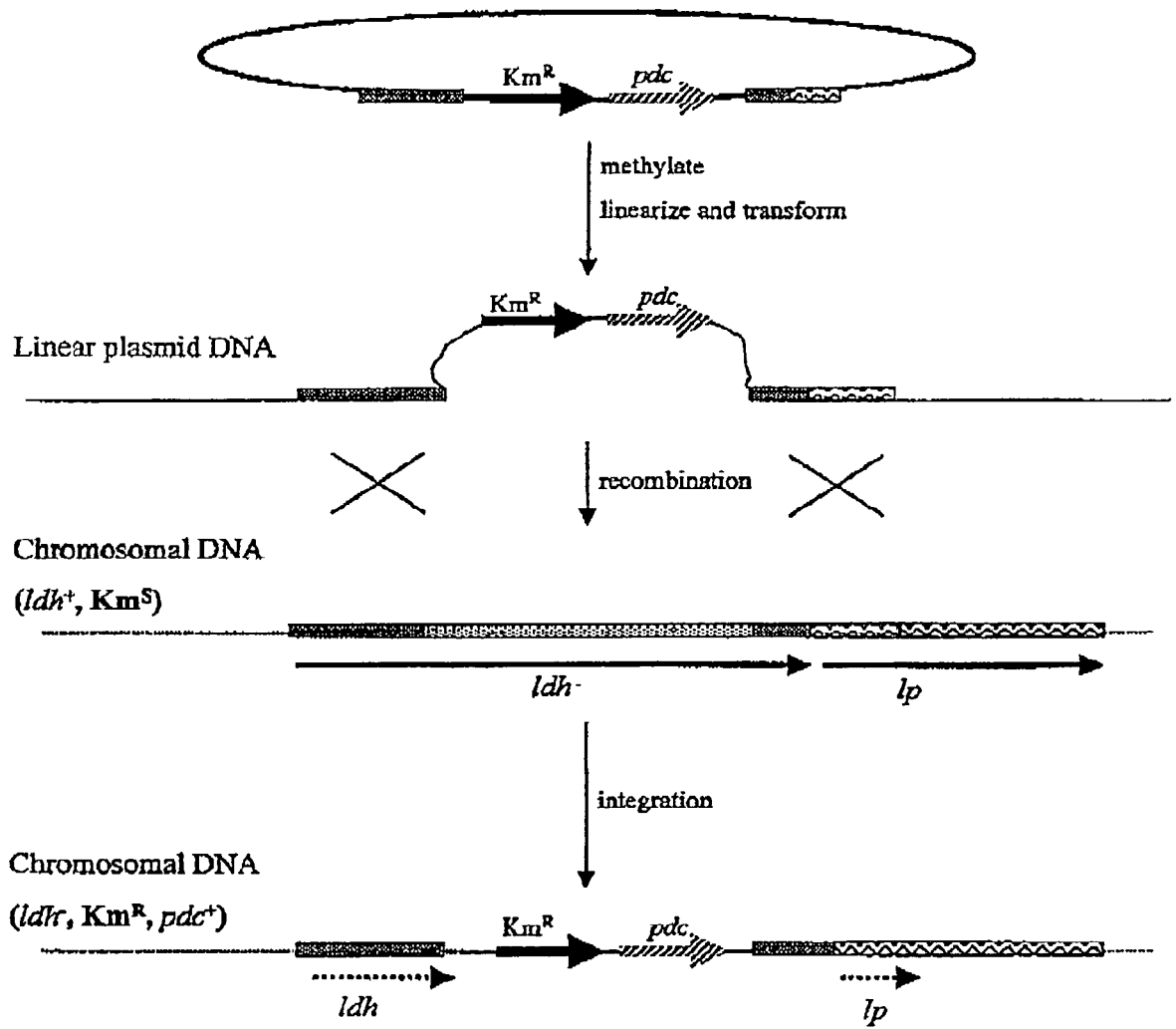
FIG. 5 is a schematic representation illustrating the method of LDH gene inactivation and heterologous gene expression by double crossover recombination.

Double-Crossover Recombination (DCO) (FIGS. 4 & 5)

DCO or replacement recombination differs from SCO in that it results in integration of only one copy of the target DNA and typically, a region of chromosomal DNA is replaced by another region, either foreign DNA or mutationally altered homologous DNA. The target DNA (kanamycin marker) was flanked on either side by mutationally altered fragments of the ldh gene in plasmid pUC-IC (a non-replicative vector based on pUC18). The vector was first methylated (in vivo) and then linearised at a site outside the flanking region (this prevents SCO). The methylated, linearised plasmid DNA was then transformed into strain LN and integrants were selected using kanamycin.

This technique has also be used to inactivate ldh and integrate a copy of the pdc gene into the chromosome simultaneously (FIG. 5) and can be applied to other genes of interest.

EXAMPLE 10

PDC Expression

In the expression plasmid pBST22-zym, the pdc gene from Z. mobilis is under the control of the ldh promoter sequence from B. stearothermophilus NCA1503 (FIG. 6). This plasmid was transformed into strain TN to form TN-P1. Although PDC improved cell growth, pdc expression and subsequent enzyme activity was relatively wreak and there was only a small increase in ethanol yield. In addition, PDC activity is sensitive to temperature and rapidly declined at growth temperatures greater than 60° C.

Therefore, we increased expression of pdc by firstly replacing the ldh promoter from B. stearothermophilus NCA 1503 with the ldh promoter sequence from Bacillus sp. LN (FIG. 6). The pdc gene under the control of ldh promoter from strain LN (construct 2) was subcloned into pFC1 to form plasmid pFC1-PDC1 (FIG. 9). Plasmid pFC1 is a shuttle vector that contains a Gram-positive and Gram-negative replicon and confers resistance to ampicillin and tetracycline. This plasmid was transformed into strain TN to form TN-P3.

Strain Performance

TN-P3 produces significantly more ethanol than the untransformed control strain TN.

| Strain | Ethanol Concentration |
|--------|----------------------|
| TN     | 21.5 mM              |
| TN-P1  | 24.0 mM              |
| TN-P3  | 39.5 mM              |

The strains were cultured in a culture medium containing JSD supplemented with 50 mM PIPES buffer and 2% glucose at 54° C. for 24 hours. TN-P1 and TN-P3 cultures were supplemented with kanamycin (12 μg/ml) and tetracycline (10 μg/ml), respectively.

The thermostability of pdc can be improved by cloning an alternative pdc gene, encoding a more thermostable PDC enzyme, from Saccharomyces cerevisiae. This gene, referred to as pdc5 will also be under the control of the ldh promoter from strain LN (see FIG. 9, construct 3). The construct will be cloned into pFC1 and the resulting plasmid pFC1-PDC5 will be transformed into strain TN.

Development of an Artificial PDC Operon

An artificial PDC operon can be constructed using interchangeable gene sequences from the ldh promoter, pdc genes from Z. mobilis and the yeast Saccharomyces cerevisiae, and adh from LN (see FIG. 10).

1) pdc expression should be increased when the ldh promoter from B. stearothermophilus NCA1503 is replaced by the ldh promoter from LN and will result in higher ethanol yields.
2) the ethanol yields should be increased further if adh from LN is co-expressed with pdc from Z. mobilis in a PDC operon Ethanol yields should be close to theoretical values of 0.5 g ethanol/g sugar.
3) the thermostability of pdc may be increased above 64° C. if the Z. mobilis pdc gene is replaced by the pdc5 gene from S. cerevisiae. This will increase the growth temperature from 64 to 70° C.

Integration of the PDC Operon into Strain LN-D11

By fusing the PDC operon to the insertion element sequence (first identified in the ldh gene from TN) several copies of the PDC operon can be introduced into multiple sites on the chromosome increasing both the stability and gene dosage.

This expression strategy may also be used for other genes of interest.

The invention claimed is:

1. An isolated *Bacillus* bacterial strain selected from the group consisting of: Strain LN having NCIMB accession number 41038; TN having NCIMB accession number 41039; LN-S (J8) having NCIMB accession number 41040; and LN-D having NCIMB accession number 41041.

2. An isolated *Bacillus* bacterial strain LN having NCIMB accession number 41038.

3. An isolated *Bacillus* bacterial strain LN-D having NCIMB accession number 41041.

4. A method of producing ethanol comprising culturing a bacterial strain according to claim 1, 2 or 3 under suitable conditions.

5. The method according to claim 4 in which the culturing is at a temperature between 40-75° C.

6. The method according to claim 5 in which the culturing is at a temperature of 52-65° C.

7. The method according to claim 5 in which the culturing is at a temperature of 60-65° C.

* * * * *

SEQUENCE LISTING

<160> NUMBER OF SEQ ID NOS: 5

<210> SEQ ID NO 1
<211> LENGTH: 24
<212> TYPE: DNA
<213> ORGANISM: Z. mobilis

<400> SEQUENCE: 1
gagctcgcaa tgagttatac tgtc                                           24

<210> SEQ ID NO 2
<211> LENGTH: 22
<212> TYPE: DNA
<213> ORGANISM: Z. mobilis

<400> SEQUENCE: 2
ggatccctag aggagcttgt ta                                             22

<210> SEQ ID NO 3
<211> LENGTH: 23
<212> TYPE: DNA
<213> ORGANISM: Bacillus LN

<400> SEQUENCE: 3

```
ggatccggca atctgaaagg aag                                              23

<210> SEQ ID NO 4
<211> LENGTH: 21
<212> TYPE: DNA
<213> ORGANISM: Bacillus LN

<400> SEQUENCE: 4
gagctctcat cctttccaaa a                                                21

<210> SEQ ID NO 5
<211> LENGTH: 301
<212> TYPE: DNA
<213> ORGANISM: Bacillus LN

<400> SEQUENCE: 5
agggcaatct gaaaggaagg gaaaattcct ttcggattgt cctttttagtt attttatgg      60 ggagtgaata ttatataggc attacggaaa tgataatggc agagtttttt catttattag    120
actgcttgat gtaattggat gtgatgatac aaaaataatg ttgtgtaaac aaaatgttaa    180
caaaaaagac aaatttcatt catagttgat acttcataaa cattctcaaa taatccacaa    240
tatatcaatg tatgagcagt ttcacaaatt catttttggg aaaggatgac agacagcgat    300
g                                                                    301
```